US007463928B2

(12) United States Patent
Lee et al.

(10) Patent No.: US 7,463,928 B2
(45) Date of Patent: Dec. 9, 2008

(54) IDENTIFYING COMBINATIONS OF ELECTRODES FOR NEUROSTIMULATION THERAPY

(75) Inventors: Michael T. Lee, Minnetonka, MN (US); Steven M. Goetz, Brooklyn Center, MN (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 959 days.

(21) Appl. No.: 10/424,194

(22) Filed: Apr. 25, 2003

(65) Prior Publication Data

US 2004/0215288 A1    Oct. 28, 2004

(51) Int. Cl.
*A61N 1/00* (2006.01)
(52) U.S. Cl. ..................................... 607/58
(58) Field of Classification Search .......... None
See application file for complete search history.

(56) References Cited

U.S. PATENT DOCUMENTS

| 4,515,158 | A | 5/1985 | Patrick et al. |
|---|---|---|---|
| 4,549,548 | A | 10/1985 | Wittkampf et al. |
| 5,033,469 | A | 7/1991 | Brodard |
| 5,443,486 | A | 8/1995 | Hrdlicka et al. |
| 5,775,331 | A | 7/1998 | Raymond et al. |
| 5,893,883 | A | 4/1999 | Torgerson et al. |
| 5,938,690 | A | 8/1999 | Law et al. |
| 6,044,303 | A | 3/2000 | Agarwala et al. |
| 6,052,624 | A | 4/2000 | Mann |
| 6,393,325 | B1 | 5/2002 | Mann et al. |
| 6,440,090 | B1 | 8/2002 | Schallhorn |

(Continued)

FOREIGN PATENT DOCUMENTS

EP    0 730 882    9/1996

(Continued)

OTHER PUBLICATIONS

International Search Report for PCT/US2004/002155, filed Jan. 27, 2004.

(Continued)

*Primary Examiner*—Carl H. Layno
*Assistant Examiner*—Jon-Eric C. Morales
(74) *Attorney, Agent, or Firm*—Shumaker & Sieffert, PA

(57) ABSTRACT

A programmer allows a clinician to identify combinations of electrodes from within an electrode set implanted in a patient that enable delivery of desirable neurostimulation therapy by an implantable medical device. The programmer executes an electrode combination search algorithm to select combinations of electrodes to test in a non-random order. According to algorithms consistent with the invention, the programmer may first identify a position of a first cathode for subsequent combinations, and then select electrodes from the set to test with the first cathode as anodes or additional cathodes based on the proximity of the electrodes to the first cathode. The programmer may store information for each combination tested, and the information may facilitate the identification of desirable electrode combinations by the clinician. The clinician may create neurostimulation therapy programs that include identified desirable program combinations.

45 Claims, 10 Drawing Sheets

U.S. PATENT DOCUMENTS

| | | | |
|---|---|---|---|
| 6,473,653 B1 * | 10/2002 | Schallhorn et al. | 607/116 |
| 6,480,743 B1 | 11/2002 | Kirkpatrick et al. | |
| 6,587,724 B2 * | 7/2003 | Mann | 607/30 |
| 2002/0169484 A1 | 11/2002 | Mathis et al. | |
| 2003/0004549 A1 | 1/2003 | Hill et al. | |
| 2004/0158298 A1 * | 8/2004 | Giner et al. | 607/48 |

FOREIGN PATENT DOCUMENTS

| | | |
|---|---|---|
| EP | 1 249 254 | 10/2002 |
| EP | 1304137 | 4/2003 |
| WO | WO 01/83028 A1 | 11/2001 |
| WO | WO 01/93953 | 12/2001 |
| WO | WO 02/09808 | 2/2002 |
| WO | WO 04/041352 | 5/2004 |

OTHER PUBLICATIONS

Written Opinion dated Mar. 3, 2005, International Application No. PCT/US2004/012838.

Notification of Transmittal of the International Preliminary Report on Patentability for PCT/US2004/002155 dated Jun. 30, 2005 (8 pgs.).

Notification of Transmittal of the International Preliminary Report on Patentability for PCT/US2004/012838 dated Aug. 30, 2005 (9 pgs.).

Office Action dated Dec. 13, 2007 for U.S. Appl. No. 11/404,069 (7 pgs.).

* cited by examiner

FIG. 6A (120)

| 12 | 13 |
|----|----|
| 8  | 9  |
| 4  | 5  |
| —  | 1  |
| 2  | 3  |
| 6  | 7  |
| 10 | 11 |
| 14 | 15 |

FIG. 6B (130)

| 13 | 12 |
|----|----|
| 9  | 8  |
| 5  | 4  |
| 1  | —  |
| 3  | 2  |
| 7  | 6  |
| 11 | 10 |
| 15 | 14 |

FIG. 6C (140)

| 6 |
|---|
| 4 |
| 2 |
| — |
| 1 |
| 3 |
| 5 |
| 7 |

FIG. 6D (150)

| 13 | 14 |
|----|----|
| 9  | 10 |
| 5  | 6  |
| +  | 4  |
| —  | 3  |
| 1  | 2  |
| 7  | 8  |
| 11 | 12 |

200

| 11 | 10 |
|---|---|
| 7 | 6 |
| 4 | 2 |
| − | + |
| 3 | 1 |
| 8 | 5 |
| 12 | 9 |
| 14 | 13 |

|  | 11 |
|---|---|
|  | 8 |
| + | 5 |
|  | 4 |
| − | 3 |
| 1 | 2 |
| 6 | 7 |
| 9 | 10 |

| 3 |
|---|
| 2 |
| 1 |
| − |
| + |
|  |
|  |
|  |

FIG. 6K

IDENTIFYING COMBINATIONS OF ELECTRODES FOR NEUROSTIMULATION THERAPY

TECHNICAL FIELD

The invention relates to neurostimulation therapy and, more particularly, to selection and configuration of electrodes used to deliver neurostimulation therapy to a patient.

BACKGROUND

Implantable medical devices may be used to deliver neurostimulation therapy to patients to treat a variety of symptoms or conditions such as chronic pain, tremor, Parkinson's disease, epilepsy, incontinence, or gastroparesis. An implantable medical device may deliver neurostimulation therapy via leads that include electrodes located proximate to the spinal cord, pelvic nerves, or stomach, or within the brain of a patient. In general, the implantable medical device delivers neurostimulation therapy in the form of electrical pulses.

A clinician may select values for a number of programmable parameters in order to define the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient. The clinician may also select as parameters particular electrodes within an electrode set to be used to deliver the pulses, and the polarities of the selected electrodes. A group of parameter values may be referred to as a program in the sense that they drive the neurostimulation therapy to be delivered to the patient.

The process of selecting values for the parameters that provide adequate results can be time consuming, and may require a great deal of trial and error before a "best" program is discovered. The "best" program may be a program that is better in terms of clinical efficacy versus side effects experienced and power consumption than other programs tested. As a portion of the overall parameter selection process, the process of selecting electrodes and the polarities of the electrodes can be particularly time-consuming and tedious. The clinician may need to test all possible combinations of electrodes within the set implanted in the patient, or a significant portion thereof, in order to identify a "best" combination of electrodes and their polarities. In some cases, the clinician may test combinations by manually specifying each combination to test based on intuition or some idiosyncratic methodology, and recording notes on the efficacy and side effects of each combination after delivery of stimulation via that combination. In this manner, the clinician is able to later compare and select from the tested combinations. As an example illustrating the magnitude of such a task, implantable medical devices commonly deliver spinal cord stimulation therapy (SCS) to a patient via two leads that include eight electrodes per lead and provide well over one million potential electrode combinations.

SUMMARY

In general, the invention is directed to techniques that may be employed by a programming device to allow a clinician or patient to identify combinations of electrodes from within an electrode set implanted in a patient that enable delivery of desirable neurostimulation therapy by an implantable medical device. The programmer may execute an electrode combination search algorithm to select combinations of electrodes to test in a non-random order. By selecting combinations in a non-random order, the programmer may allow the clinician or patient to more quickly identify desirable electrode combinations.

According to algorithms consistent with the invention, the programmer may identify a position of a first cathode electrode for subsequent combinations, and then select electrodes from the electrode set to test with the first cathode as anodes or additional cathodes based on the proximity of the electrodes to the first cathode. The programmer may identify a first position within the electrode set, which may be a central position within the electrode set, and control the implantable medical device to test the electrode located at that position as the first cathode. The programmer may then test additional electrodes from within the set as the first cathode in an order based on proximity to the first cathode.

The programmer may receive input from the clinician or patient indicating which tested electrode is the first cathode, and then control the implantable medical device to test other electrodes of the set in combination with the first cathode. Undesignated electrodes may be tested as anodes and additional cathodes in an order based on proximity to the first cathode. In some cases, only a subset of the undesignated electrodes may be tested to avoid testing redundant electrode combinations, i.e., electrode combinations that would produce substantially the same current flow as an electrode combination already tested.

The programmer may store information for each combination tested, and the information may facilitate the identification of desirable electrode combinations by the clinician. For example, the programmer may present a list of tested combinations and their associated information, and the list may be ordered according to the information. The clinician may create neurostimulation therapy programs that include identified desirable program combinations.

In one embodiment, the invention is directed to a method in which a first electrode of a set of electrodes implanted in a patient is selected to be included in a combination of electrodes for use in delivery of neurostimulation to the patient. The first electrode may be a cathode for the combination. A sequence of additional electrodes of the set to test for inclusion in the combination is automatically selected according to locations of the additional electrodes relative to the first electrode. The additional electrodes may be tested for inclusion of one of the additional electrodes as an anode for the combination.

In another embodiment, the invention is directed to a computer-readable medium containing instructions. The instructions cause a programmable processor to select a first electrode of a set of electrodes implanted in a patient to include in a combination of electrodes for use in delivery of neurostimulation to the patient. The instructions also cause a processor to automatically select a sequence of additional electrodes within the set to test for inclusion in the combination according to locations of the additional electrodes relative to the first electrode.

In another embodiment, the invention is directed to a device that includes a processor. The processor selects a first electrode of a set of electrodes implanted in a patient to include in a combination of electrodes for delivery of neurostimulation therapy to the patient. The processor also automatically selects a sequence of additional electrodes to test for inclusion in the combination according to locations of the additional electrodes relative to the first electrode. The device may be a programming device associated with one of a clinician and the patient.

In another embodiment, the invention is directed to a method in which a search algorithm is executed to control an implantable medical device to test combinations of electrodes in an order that is based on the proximity of the electrodes of the combinations to a central position within the set. Information identifying at least one of the tested combinations is stored as part of a neurostimulation therapy program that defines neurostimulation therapy to be delivered to the patient by the implantable medical device.

The invention may provide a number of advantages. For example, the invention may allow a clinician to more quickly identify desirable electrode combinations, reducing the overall amount of time the clinician spends programming neurostimulation therapy for a patient. In contrast to existing neurostimulation programming systems that present electrode combinations in a random order and idiosyncratic search methodologies employed by clinicians, programmer according to the invention may select electrode combinations in a systematic manner to test in an order such that electrode combinations that are more likely to enable desirable therapy are selected earlier in the search. Consequently, the clinician may be able to end the search before all potential electrode combinations have been tested if one or more desirable combinations have already been identified.

Even if a clinician elects to test all potential electrode combinations, e.g., if the electrode set is small enough to make testing all electrode combinations practical, the invention may reduce the time required to identify desirable electrode combinations by automating selection of each new combination to test. The invention may also avoid testing redundant combinations, i.e., combinations that are substantially equivalent to combinations already tested. Avoiding redundant combinations may further reduce the amount of time required for the search.

Additionally, the invention may improve the search process by collecting amplitude information, and rating information that is entered by the clinician or patient, for each combination tested. A programmer according to the invention may present a list of tested electrode combinations to the clinician, ordered according to one or both of the amplitude and rating information, allowing the clinician to more easily identify and select desirable combinations. A bracket of untested electrode combinations that are similar to identified electrode combinations may be used to create programs that are provided to the patient. Providing bracket programs to the patient allows the patient to experiment with the programs to "finely tune" the neurostimulation therapy provided by the implantable medical device without requiring the clinician to be involved.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIGS. 6A-6K are diagrams illustrating example matrices that illustrate positions within exemplary electrode set configurations and orders in which electrodes within such electrode sets may be tested according to electrode combination search algorithms consistent with the invention.

DETAILED DESCRIPTION

Figure 1:
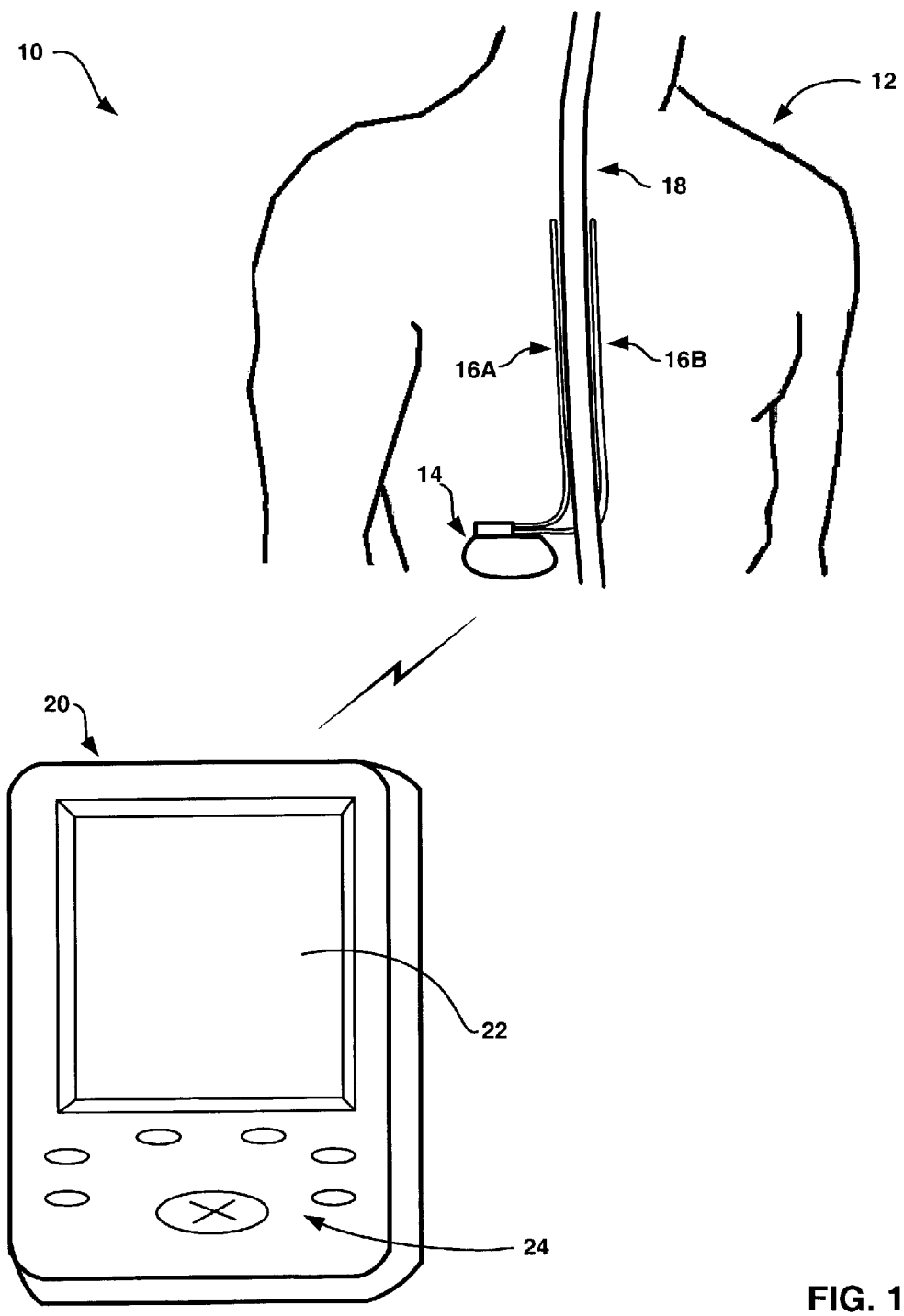
FIG. 1 is a diagram illustrating an example system for programming and delivering neurostimulation therapy.

FIG. 1 is a diagram illustrating an example system 10 for programming neurostimulation therapy for and delivering neurostimulation therapy to a patient 12. System 10 includes an implantable medical device 14 that delivers neurostimulation therapy to patient 12. IMD 14 may be an implantable pulse generator, and may deliver neurostimulation therapy to patient 12 in the form of electrical pulses.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown) or stomach (not shown), and IMD 14 may deliver neurostimulation therapy to treat incontinence or gastroparesis.

IMD 14 delivers neurostimulation therapy to patient 12 according to one or more neurostimulation therapy programs. A neurostimulation therapy program may include values for a number of parameters, and the parameter values define the neurostimulation therapy delivered according to that program. In embodiments where IMD 14 delivers neurostimulation therapy in the form of electrical pulses, the parameters may include pulse voltage or current amplitudes, pulse widths, pulse rates, and the like. Further, each of leads 16 includes electrodes (not shown in FIG. 1), and the parameters for a program may include information identifying which electrodes have been selected for delivery of pulses according to the program, and the polarities of the selected electrodes.

A selected subset of the electrodes located on leads 16 and the polarities of the electrodes of the subset collectively define an "electrode combination." Electrode combinations refer to combinations of single or multiple cathode electrodes and single or multiple anode electrodes. Stimulation current flows between the cathodes and anodes for delivery of neurostimulation therapy.

System 10 also includes a programmer 20. Programmer 20 may, as shown in FIG. 1, be a handheld computing device. Programmer 20 includes a display 22, such as a LCD or LED display, to display information to a user. Programmer 20 may also include a keypad 24, which may be used by a user to interact with programmer 20. In some embodiments, display 22 may be a touch screen display, and a user may interact with programmer 20 via display 22. A user may also interact with programmer 20 using peripheral pointing devices, such as a stylus or mouse. Keypad 24 may take the form of an alphanumeric keypad or a reduced set of keys associated with particular functions.

A clinician (not shown) may use programmer 20 to program neurostimulation therapy for patient 12. In particular, the clinician may use programmer 20 to create neurostimulation therapy programs. As part of the program creation process, programmer 20 allows the clinician to identify electrode combinations that enable IMD 14 to deliver neurostimulation therapy that is desirable in terms of, for example, symptom relief, coverage area relative to symptom area, and side effects. Programmer 20 may also allow the clinician to identify electrode combinations that enable IMD 14 to deliver effective neurostimulation therapy with desirable device performance characteristics, e.g., low battery consumption.

Programmer 20 controls IMD 14 to test electrode combinations in order to allow a clinician to identify desirable combinations in an efficient manner. As will be described in greater detail below, programmer 20 may select electrode combinations to test based on an electrode combination search algorithm. In particular, according to such an algorithm, programmer 20 may first control IMD 14 to test one or more electrodes to identify the electrode which will act as a first cathode electrode, and then control IMD 14 to test combinations that include the first cathode in an order that is based on the proximity of other electrodes in the combination to the first cathode.

By controlling IMD 14 to test electrode combinations in such an order, programmer 20 may allow the clinician to more quickly identify desirable electrode combinations, reducing the overall amount of time the clinician spends programming neurostimulation therapy for patient 12. In contrast to existing neurostimulation programming systems that present electrode combinations in a random order and idiosyncratic search methodologies employed by clinicians, programmer 20 may select electrode combinations to test in an order such that electrode combinations that are more likely to enable desirable therapy are selected earlier in the search. Consequently, the clinician may be able to end the search before all potential electrode combinations have been tested if one or more desirable combinations have already been identified, saving the amount clinician and patient time required to achieve an efficacious electrode combination.

Even if the clinician elects to test all potential electrode combinations, e.g., if the electrode set is small enough to make testing all electrode combinations practical, programmer 20 may reduce the time required to identify desirable electrode combinations by automating selection of each new combination to test. Additionally, programmer 20 may improve the search process by collecting amplitude and rating information for each combination tested. As will be described in greater detail below, programmer 20 may present a list of electrode combinations to the clinician, ordered according to one or both of the amplitude and rating information, allowing the clinician to more easily identify and select desirable combinations.

In order to control IMD 14 to test electrode combinations, programmer 20 may communicate with IMD 14 via telemetry techniques known in the art. For example, programmer 20 may communicate with IMD 14 via an RF telemetry head (not shown). Information identifying desirable combinations of electrodes identified by the clinician may be stored as part of neurostimulation therapy programs. Neurostimulation therapy programs created by the clinician using programmer 20 may be transmitted to IMD 14 via telemetry, and/or may be transmitted to another programmer (not shown), e.g., a patient programmer, that is used by patient 12 to control the delivery of neurostimulation therapy by IMD 14.

Figure 2:
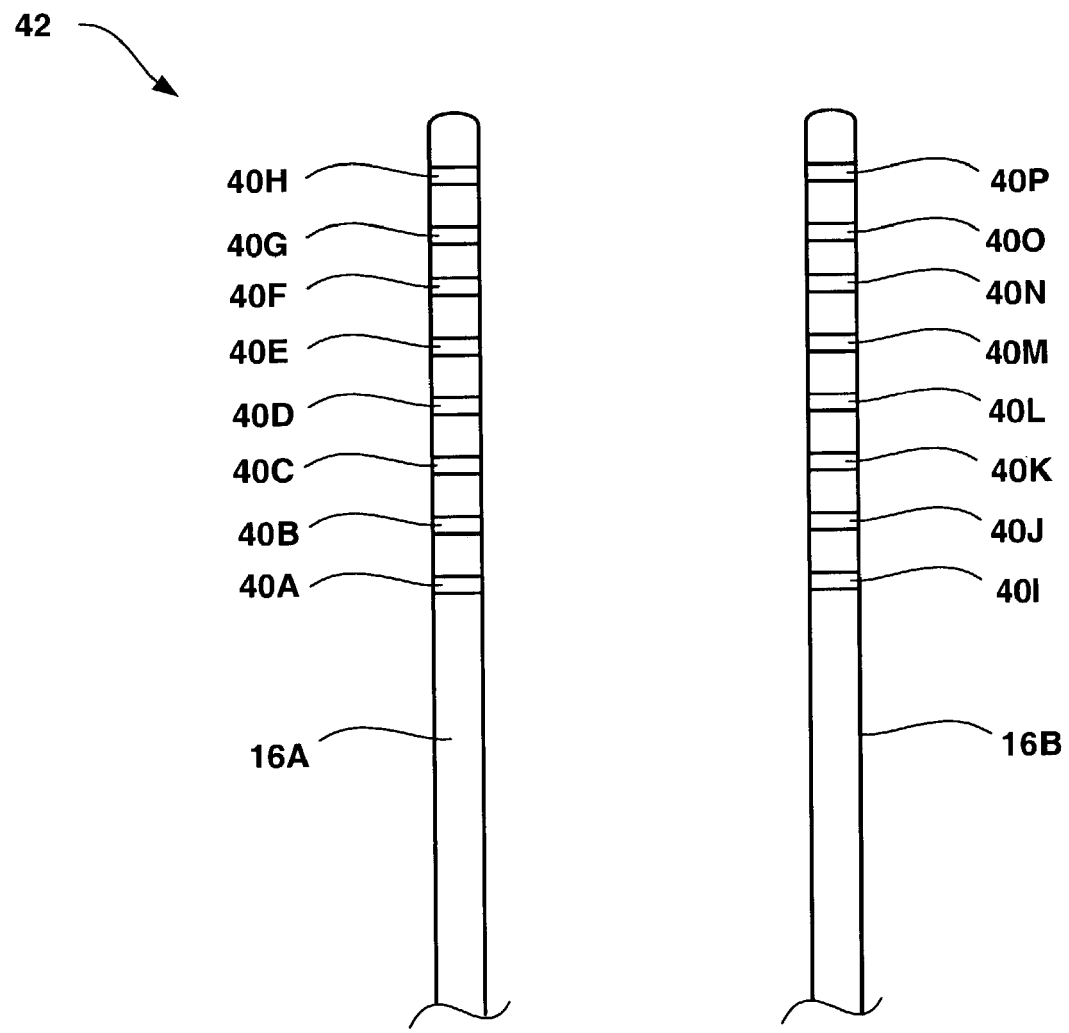
FIG. 2 is a diagram illustrating an example electrode set that may be implanted within the patient.

FIG. 2 is a block diagram illustrating an example configuration of leads 16. In the example configuration, lead 16A includes electrodes 40A-H, and lead 16B includes electrodes 40I-P. Electrodes 40A-P (collectively "electrodes 40") may be ring electrodes.

Electrodes 40 collectively form an electrode set 42 implanted within patient 12. As shown in FIG. 2, electrode set 42 includes eight electrodes on each of the two leads 16, which, as shown in FIG. 1, are implanted such that they are substantially parallel to each other and spinal cord 18, on substantially opposite sides of spinal cord 18, at approximately the same height relative to spinal cord 18, and oriented such that the distal ends of leads 16 are higher relative to the spinal cord than the proximal ends of leads 16. Therefore, the illustrated configuration of electrode set 42 may be described as a two-by-eight, side-by-side, upwardly oriented configuration.

Such a configuration is commonly used to provide SCS therapy. However, programmer 20 may be used to identify desirable combinations of electrodes within electrode sets that are configured in any way, and used to provide any type neurostimulation therapy. For example, a single lead including four or eight electrodes, two leads including four electrodes per lead, in-line leads, and offset leads, all of which may be oriented in any manner relative to patient 12, provide electrode set configurations that may be searched by programmer 20.

IMD 14 (FIG. 1) may deliver neurostimulation via any combination of electrodes 40. IMD 14 may independently activate each electrode 40 of set 42 to act as a cathode or anode for a combination, and each combination will include at least one cathode and at least one anode. In some embodiments, a combination may include a single electrode 40 acting as the cathode, with a can of IMD 14, i.e., the IMD housing, acting as the anode for the combination.

In an electrode combination, electrons flow from the one or more electrodes acting as anodes for the combination to the one or more electrodes acting as cathodes for the combination. The current between anodes and cathodes may stimulate neurons between and proximate to the anodes and cathodes. Generally speaking, an electrode combination enables desirable neurostimulation therapy when current is delivered in a direction and with an intensity sufficient to stimulate specific neurons or a sufficient number of specific neurons to alleviate a symptom without causing unacceptable side effects. Further, an electrode combination enables desirable neurostimulation therapy when the symptom is alleviated without resorting to undesirably high pulse amplitudes.

As mentioned above, programmer 20 selects individual electrodes 40 or electrode combinations to test to allow a clinician to identify desirable electrode combinations according to an electrode search algorithm. Programmer 20 may select an appropriate search algorithm based on the configuration of electrode set 42, and may select electrodes 40 or electrode combinations based on the selected search algorithm. Programmer 20 controls IMD 14 to test a selected electrode 40 or electrode combination by controlling IMD 14 to deliver neurostimulation via the selected electrode 40 or combination.

Programmer 20 may first control IMD 14 to test one or more of electrodes 40 individually to identify the individual electrode or electrodes 40 which will act as a first cathode. Generally, a clinician implants leads 16 in a location such that the center of electrode set 42 is proximate to an area that the clinician believes should be stimulated in order to alleviate symptoms. Therefore, programmer 20 may test electrodes 40 as the first cathode in an order such that electrodes 40 located centrally within electrode set 42, e.g., electrodes 40D-E and 40L-M illustrated in FIG. 2, are tested before peripherally located electrodes. If the clinician's estimation of the target region is inaccurate, programmer 20 will continue to test individual electrodes 40 in such an order until one of the electrodes 40 that enables desirable neurostimulation therapy when activated as the first cathode is identified. Initially locating a first cathode provides a "coarse" optimization of electrode combinations, allowing programmer 20 and the clinician to quickly identify the general area to which neurostimulation therapy should be delivered.

Programmer 20 may then control IMD 14 to test electrode combinations that include the first cathode. Programmer 20 may control IMD 14 to try different ones of electrodes 40 as the first anode in a pair with the first cathode, and may add additional anodes and/or cathodes. Programmer 20 may control IMD 14 to test remaining electrodes 40 as first anodes, and additional anodes or cathodes, in an order that is based on the proximity of the remaining electrodes 40 to the electrode 40 acting as the first cathode for the electrode combination. The order may be based on decreasing proximity of the remaining electrodes 40 to the electrode acting as the first cathode, e.g., electrodes will be tested in order of increasing distance from the first cathode.

Generally, electrode combinations that include cathodes and anodes in closer proximity may be more likely to enable desirable neurostimulation therapy. Therefore, by testing electrode combinations in an order based on decreasing proximity of the other electrodes 40, programmer 20 provides a "fine" optimization of electrode combinations, allowing the clinician to more quickly identify electrode combinations that enable more desirable neurostimulation therapy than the initial combination including the first cathode and the first location of the first anode. With this approach, the search for electrode combinations may proceed in a pattern or "orbit" in close proximity about an initially selected cathode or cathodes, and then extend outward into a more distant orbit as the search continues.

Figure 3:
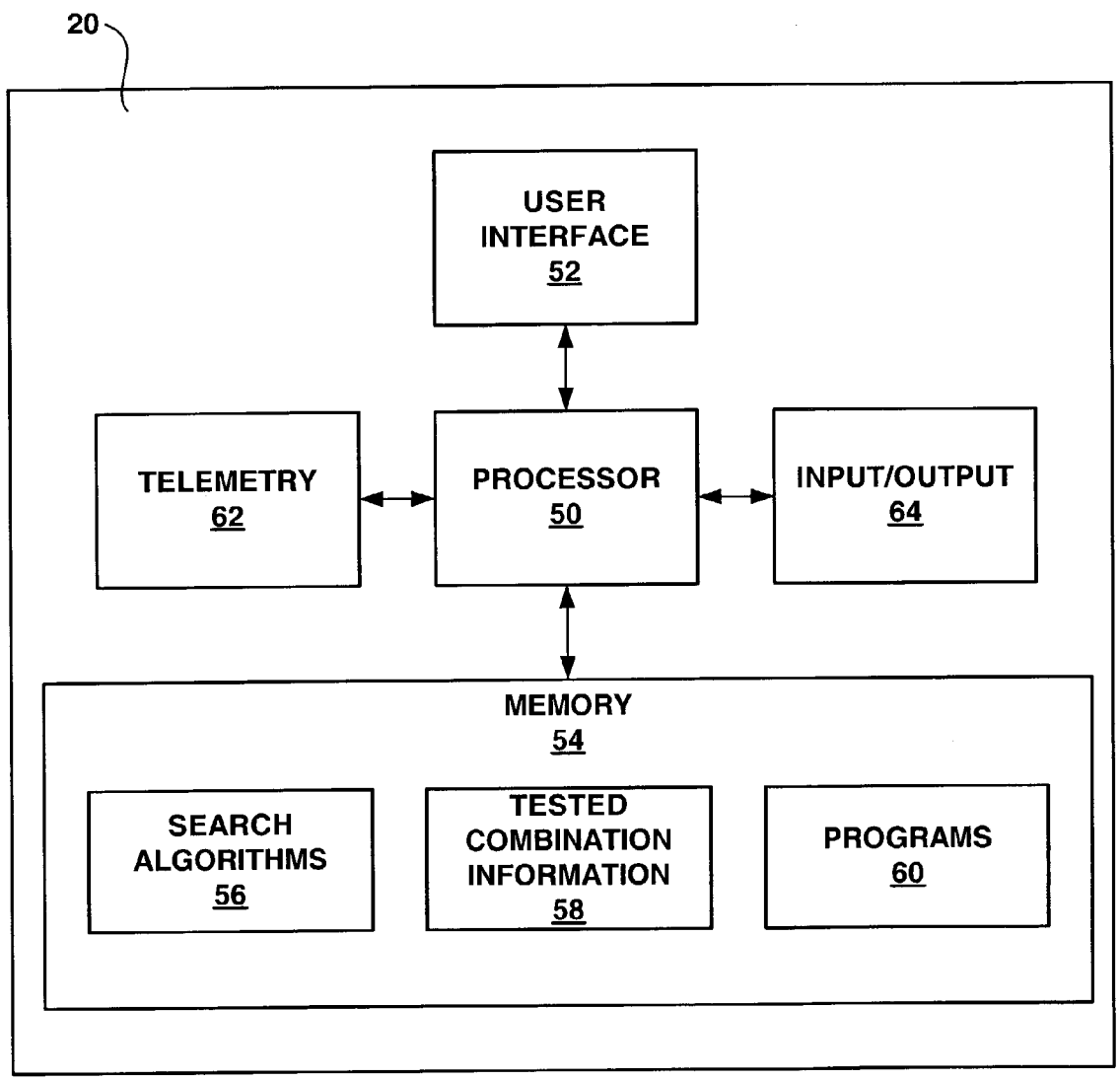
FIG. 3 is a block diagram illustrating an example programming device that allows a user to identify desirable electrode combinations for neurostimulation therapy programs.

FIG. 3 is a block diagram illustrating an example configuration of programmer 20. A clinician may interact with a processor 50 via a user interface 52 in order to identify electrode combinations as described herein. User interface 52 may include display 22 and keypad 24, and may also include a touch screen or peripheral pointing devices as described above. Processor 50 may also provide a graphical user interface (GUI) via user interface 52 to facilitate interaction with a clinician. Processor 50 may include a microprocessor, a controller, a DSP, an ASIC, an FPGA, discrete logic circuitry, or the like.

Clinician programmer 20 also includes a memory 54. Memory 54 may include program instructions that, when executed by processor 50, cause clinician programmer 20 to perform the functions ascribed to clinician programmer 20 herein. For example, processor may execute a selected one of electrode combination search algorithms 56 stored within memory 54 to select individual electrodes 40 or electrode combinations to test to allow the clinician to identify desirable electrode combinations.

As will be described in greater detail below, processor 50 may collect information relating to tested electrode combinations, and store the information in memory 54 for later retrieval and review by the clinician to facilitate identification of desirable electrode combinations. Neurostimulation therapy programs 60 created by the clinician may be stored in memory 54, and information identifying electrode combinations selected by the clinician to be utilized for one of programs 60 may be stored as part of the program within memory 54. Memory 54 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Processor 50 controls IMD 14 to test selected individual electrodes 40 or electrode combinations, by controlling IMD 14 to deliver neurostimulation therapy to patient 12 via the selected individual electrodes 40 or electrode combinations via a telemetry circuit 62. Processor 50 may transmit programs 60 created by the clinician to IMD 14 via telemetry circuit 62, or to another programmer used by the patient to control delivery of neurostimulation therapy via input/output circuitry 64. I/O circuitry 64 may include transceivers for wireless communication, appropriate ports for wired communication or communication via removable electrical media, or appropriate drives for communication via removable magnetic or optical media.

Figure 4:
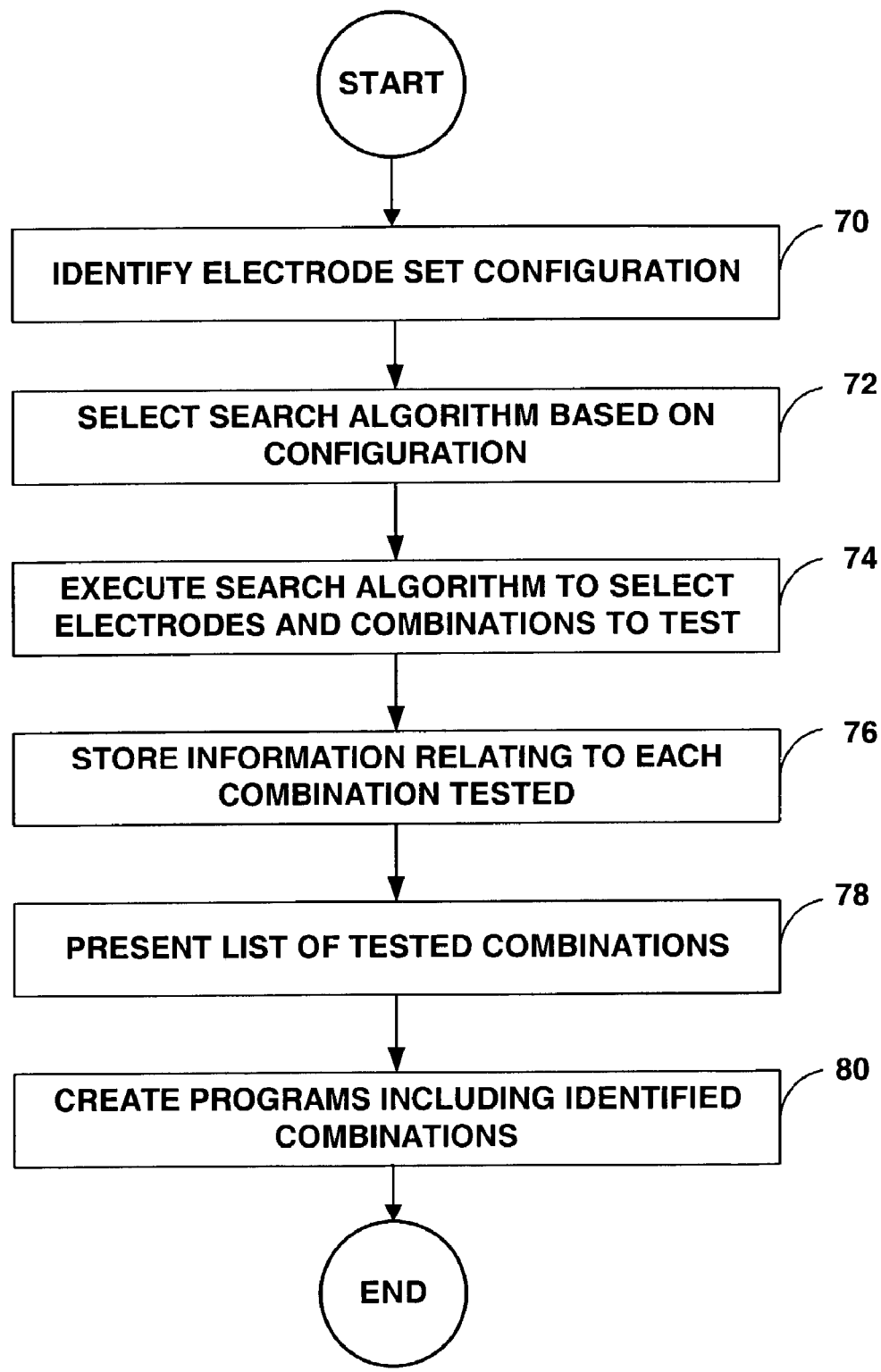
FIG. 4 is a flow diagram illustrating an example method that may be employed by a programming device to select and execute an electrode combination search algorithm according to the invention.

FIG. 4 is a flow diagram illustrating an example method that may be employed by programmer 20 to select and execute an electrode combination search algorithm according to the invention. Programmer 20, and more specifically processor 50 of programmer 20, identifies a configuration of electrode set 42 (70), and selects an electrode combination search algorithm 56 based on the configuration (72). Multiple algorithms 56 may be available for selection in order to allow programmer 20 to address differences between electrode configurations, e.g., different numbers of leads and electrodes per leads. However, each of algorithms 56 may employ the common search methodology that was discussed above, and is illustrated by FIGS. 5A and 5B discussed below.

Programmer 20 may identify the configuration of electrode set 42 by, for example, receiving input from the clinician via user interface 52 indicating the configuration. In other embodiments, information identifying the configuration of electrode set 42 may be stored in memory 54 or a memory of IMD 14 at implant. In such embodiments, programmer 20 may retrieve the information from memory 54 or from IMD 14 via telemetry circuit 62.

Programmer 20 then, as will be described in greater detail below, executes the selected search algorithm to select individual electrodes 40 and electrode combinations to test (74). When a combination is tested, programmer 20 may, as will also be described in greater detail below, store information 58 relating to that combination in memory 54. The information may include amplitude information, and/or rating information provided by one or both of the clinician and patient 12.

Programmer 20 may present a list of tested combinations to the clinician via display 22 (78). The list may include the information relating to each combination, and in some embodiments, may be ordered according to information. The list may facilitate identification of one or more desirable electrode combinations by the clinician. The clinician may create neurostimulation therapy programs 60 that include identified electrode combinations (80), and programmer 20 may store information identifying the electrode combinations selected by the clinician within programs 60 in memory 54. In some embodiments, programmer 20 may automatically select electrode combinations for inclusion in programs 60 based on the information.

Figure 5A:
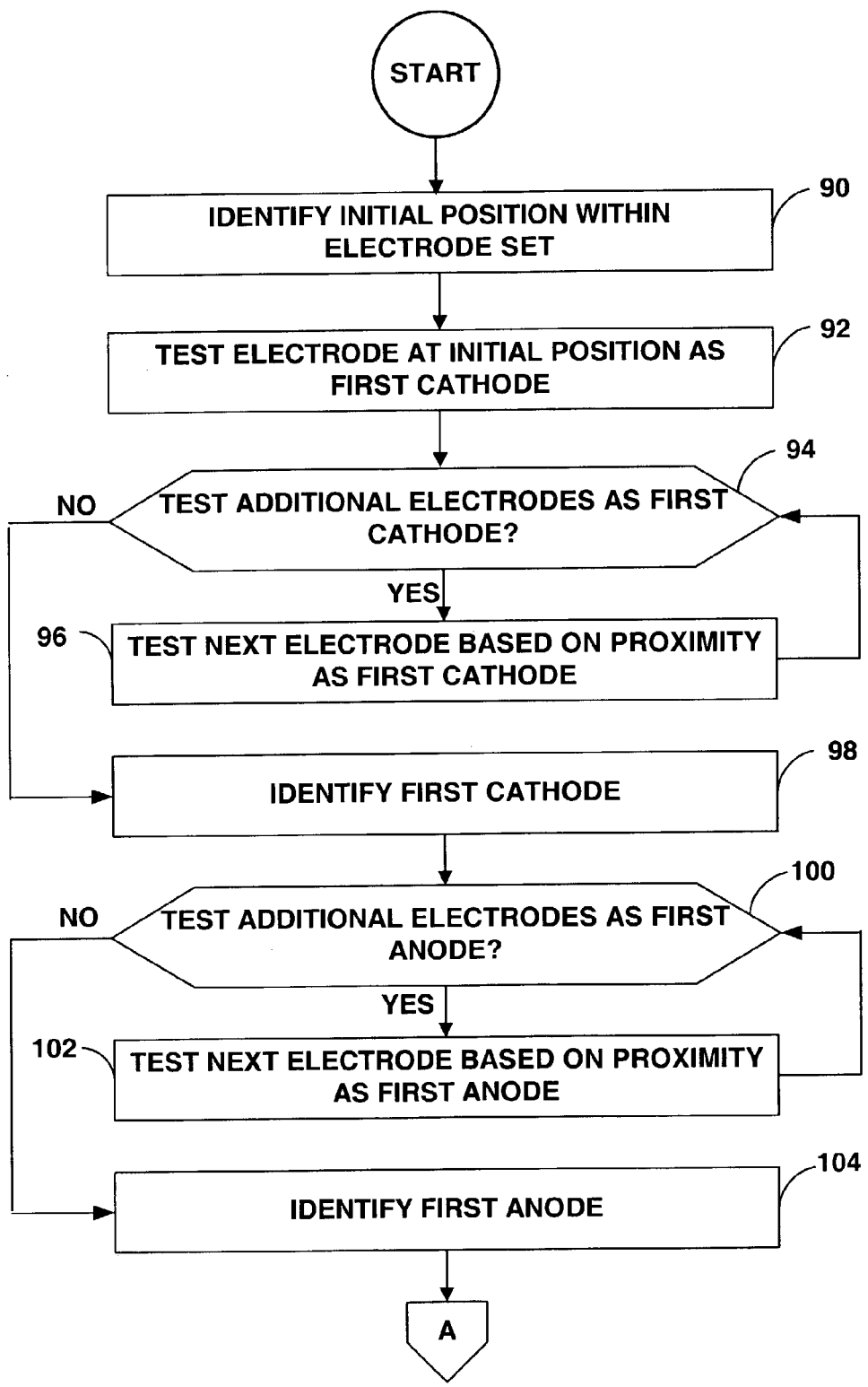
FIGS. 5A and 5B are flow diagrams illustrating an example electrode combination search algorithm that may be executed by a programming device.
Figure 5B:
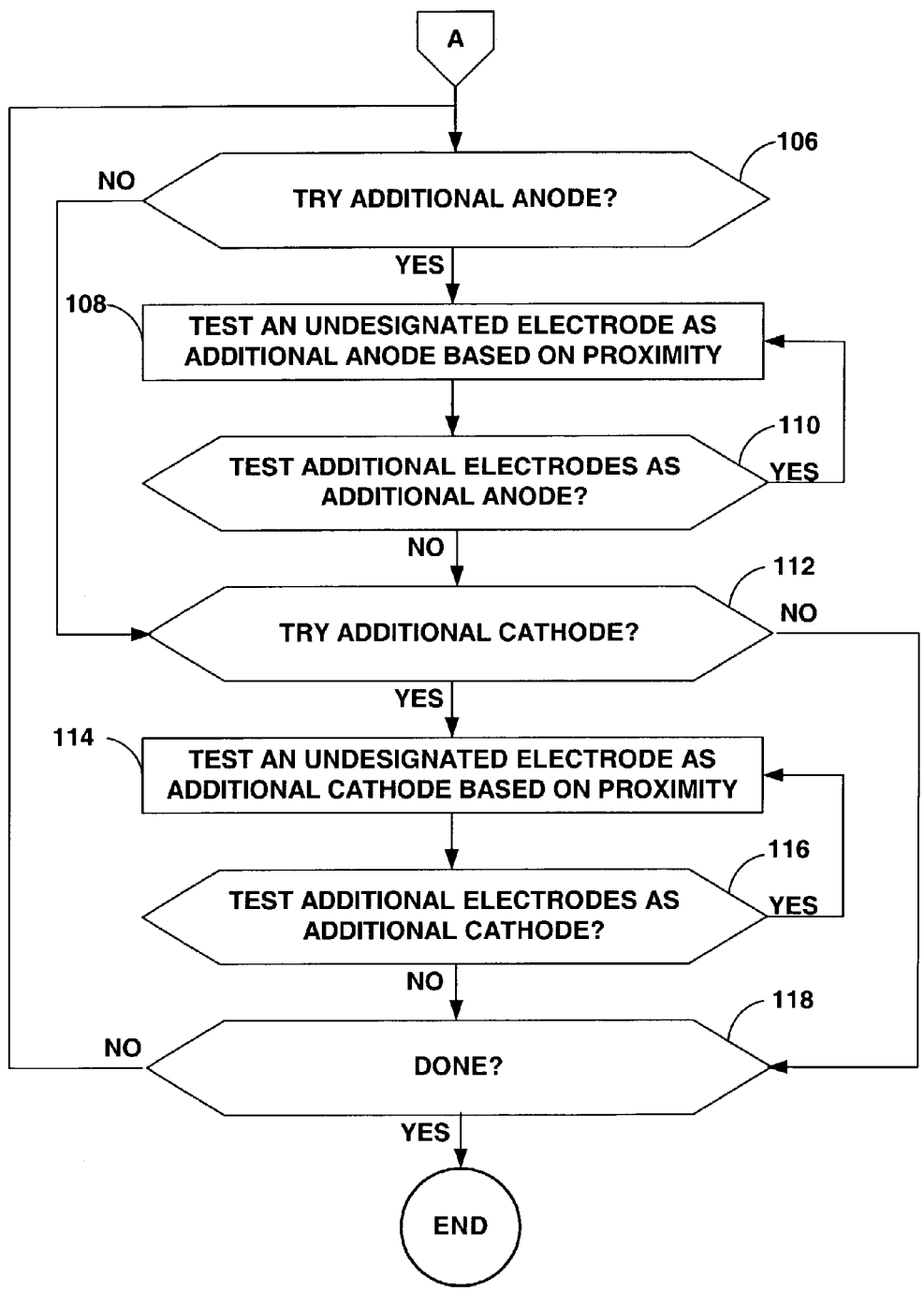

FIGS. 5A and 5B are flow diagrams illustrating an example electrode combination search algorithm that may be executed by programmer 20. As shown in FIG. 5A, programmer 20 identifies an initial position within electrode set 42 (90), and controls IMD 14 to test an electrode 40 located at the initial position as the first cathode (92). As discussed above, the initial position may be a central position within electrode set 42, and programmer 20 may identify a central position within set 42 based on the configuration of set 42. For example, programmer 20 may initially control IMD 14 to test electrode 40E (FIG. 2) as the first cathode. Alternatively, the clinician may identify the initial position or the specific electrode 40 that the clinician believes should be tested first, and programmer 20 may control IMD 14 to test the electrode 40 corresponding to input provided by the clinician.

Programmer 20 then determines whether an additional electrode 40 should be tested as the first cathode (94). Programmer 20 may prompt the clinician to indicate whether an additional electrode 40 should be tested. If the clinician is satisfied with the first electrode 40 tested, programmer 20 identifies the first electrode as the first cathode for subsequently tested combinations (98). However, if the clinician indicates that additional electrodes 40 should be tested, programmer 20 may control IMD 14 to test additional electrodes 40 of electrode set 42 in an order based on decreasing proximity to the initial position until the clinician indicates that no more electrodes 40 should be tested or all electrodes 40 of electrode set 42 have been tested (96). At that point, programmer 20 may identify the first cathode (98) either as the last electrode 40 tested, or based on input from the clinician identifying which of the tested electrodes 40 should be identified as the first cathode.

When programmer 20 controls IMD 14 to test one of electrodes 40 as the first cathode, another one of electrodes 40 adjacent to the tested electrode, or the can of IMD 14, acts as a first anode to form a cathode/anode pair. When one of the tested electrodes 40 is identified as the first cathode (96), programmer 20 may determine based on input received from the clinician whether other electrodes 40 of electrode set 42 are to be tested as the first anode (100). If the clinician indicates that no additional electrodes are to be tested as the first anode, programmer may identify the already tested electrode 40 adjacent to the first cathode as the first anode (104).

However, if the clinician indicates that additional electrodes 40 should be tested as the first anode, programmer 20 may control IMD 14 to test additional electrodes 40 of electrode set 42 in an order based on decreasing proximity to the first cathode until the clinician indicates that no more electrodes 40 should be tested or all electrodes 40 of electrode set 42 have been tested (102). At that point, programmer 20 may identify the first anode (104) either as the last electrode 40 tested, or based on input from the clinician identifying which of the tested electrodes 40 should be identified as the first anode. Each first cathode/first anode pair tested forms an electrode combination.

FIG. 5B illustrates portions of the example algorithm that enable programmer 20 and the clinician to try adding anodes and/or cathodes to the existing first cathode/first anode pair. In response to input from the clinician indicating that an additional anode or cathode should be added to an existing combination, programmer 20 selects electrodes to test as the additional anode or cathode. Where the existing combination is the first cathode/first anode pair, the resulting combinations tested may include guarded cathode or guarded anode combinations known in the art.

If programmer 20 receives an indication to try an additional anode (106), programmer 20 controls IMD 14 to test undesignated electrodes 40 of electrode set 42 in an order based on decreasing proximity to the first cathode (108) until programmer 20 receives an indication to stop testing electrodes 40 or until all electrodes 40 of electrode set 42 have been tested (110). If programmer 20 receives an indication to try an additional cathode (112), programmer 20 controls IMD 14 to test undesignated electrodes 40 of electrode set 42 in an order based on decreasing proximity to the first cathode (114) until programmer 20 receives an indication to stop testing electrodes 40 or until all electrodes 40 of electrode set 42 have been tested (116). After testing combinations that include the identified first cathode/first anode pair, and one or more additional anodes and/or one or more additional cathodes, programmer 20 may select a different first anode or first cathode based on input received from the clinician. When the clinician is satisfied that desirable electrode combinations have been identified, or when all electrode combinations have been tested, programmer 20 ends the electrode search algorithm (118), and may display a list of tested combinations as described above.

If the clinician stops the search before all possible combinations of electrodes 40 have been tested, programmer 20 may create a bracket of untested combinations that the clinician may elect to include in neurostimulation therapy programs. The bracket may consist of any number of electrode combinations, and may comprise the next n combinations that would have been tested according to the electrode combination search algorithm. By providing the clinician with a bracket, programmer 20 may allow clinician to spend less time searching for desirable electrode combinations. Specifically, the programs created using the bracket combinations may enable desirable neurostimulation therapy similar to that provided a program created with the most recently tested combination, and may be provided to patient 12 so that patient 12 can experiment with the bracket programs outside of the clinic.

Figure 6E:
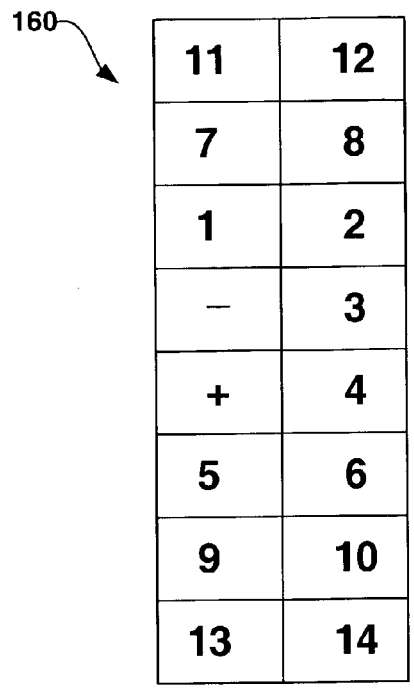
Figure 6F:
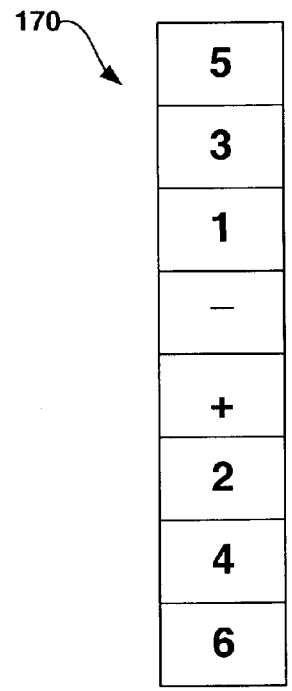
Figure 6G:
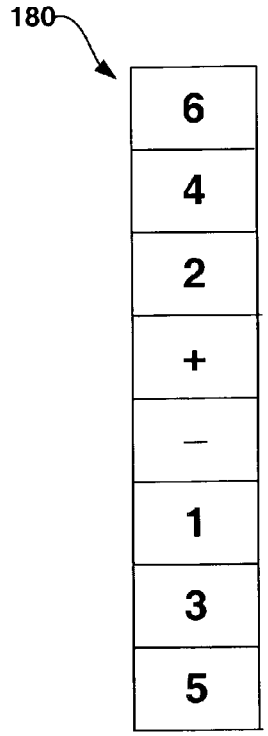
Figure 6H:
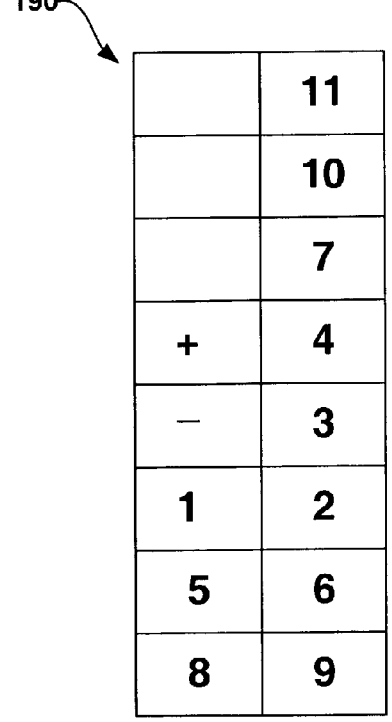

FIGS. 6A-6K are diagrams illustrating example matrices 120-220 that illustrate positions within exemplary electrode sets. FIGS. 6A-B, D-E and H-J illustrate two-by-eight matrices 120, 130, 150, 160, 190, 200 and 210 that identify positions within a two-by-eight side-by-side electrode set, such as electrode set 42. FIGS. 6C, F-G and K illustrate one-by-eight matrices 140, 170, 180 and 220 that identify positions within a one-by-eight or two-by-four in-line electrode set. More particularly, FIGS. 6A-6K illustrate orders in which programmer 20 may select electrodes within such electrode sets to test according to electrode combination search algorithms consistent with the invention, each position within a matrix indicating an electrode within an electrode set.

Matrices 120, 130 and 140 of FIGS. 6A-C illustrate orders in which programmer 20 may select electrodes to test as the first cathode. The "−" symbol in each of matrices 120, 130 and 140 indicates the initial position, i.e., the first electrode tested as the first cathode. Additional electrodes may be tested as a first cathode in the numeric orders illustrated, which illustrate examples of testing orders that are based on decreasing proximity to the initial position.

Matrices 150, 160, 170 and 180 of FIGS. 6D-G illustrate orders in which programmer 20 may select electrodes to test with an identified first cathode as the first anode. The "−" symbol in each of matrices 150, 160, 170 and 180 indicates the identified position of the first cathode. The "+" symbol in each of matrices 150, 160, 170 and 180 indicates the position of an electrode already tested with the first cathode as the first anode during the process of identifying the first cathode. Other electrodes of an electrode set corresponding to one of matrices 150, 160, 170 and 180 may be tested as a first anode in the numeric orders illustrated, which illustrate examples of testing orders that are based on decreasing proximity to the identified first cathode.

Matrices 190, 200, 210 and 220 of FIGS. 6H-K illustrate orders in which programmer 20 may select electrodes to test with an identified first cathode/first anode pair as an additional anode. The "−" symbol in each of matrices 190, 200, 210 and 220 indicates the identified position of the first cathode. The "+" symbol in each of matrices 190, 200, 210 and 220 indicates the identified position of the first anode. Programmer 20 may test other undesignated electrodes of an electrode set corresponding to one of matrices 190, 200, 210 and 220 as an additional anode in the numeric orders illustrated, which illustrate examples of testing orders that are based on decreasing proximity to the identified first cathode.

As illustrated by matrices 190, 210 and 220, programmer 20 may test only a subset of the undesignated electrodes of an electrode set. Specifically, programmer may avoid testing electrodes as an additional anode that would provide substantially the same current flow as the first cathode/first anode pair due to the orientation of the additional anode and the first cathode/first anode pair. By testing only a subset of the undesignated electrodes and avoiding redundant combinations, programmer may further shorten the time required of the clinician to identify desirable electrode combinations.

The illustrated matrices are merely exemplary. Again, programmer 20 may test electrodes within any type of electrode configuration. Further, configurations that include multiple additional anodes, or one or more additional cathodes may be tested. Whenever a cathode or anode is added, testing may be limited to a subset of undesignated electrodes in order to avoid redundant combinations.

Figure 7:
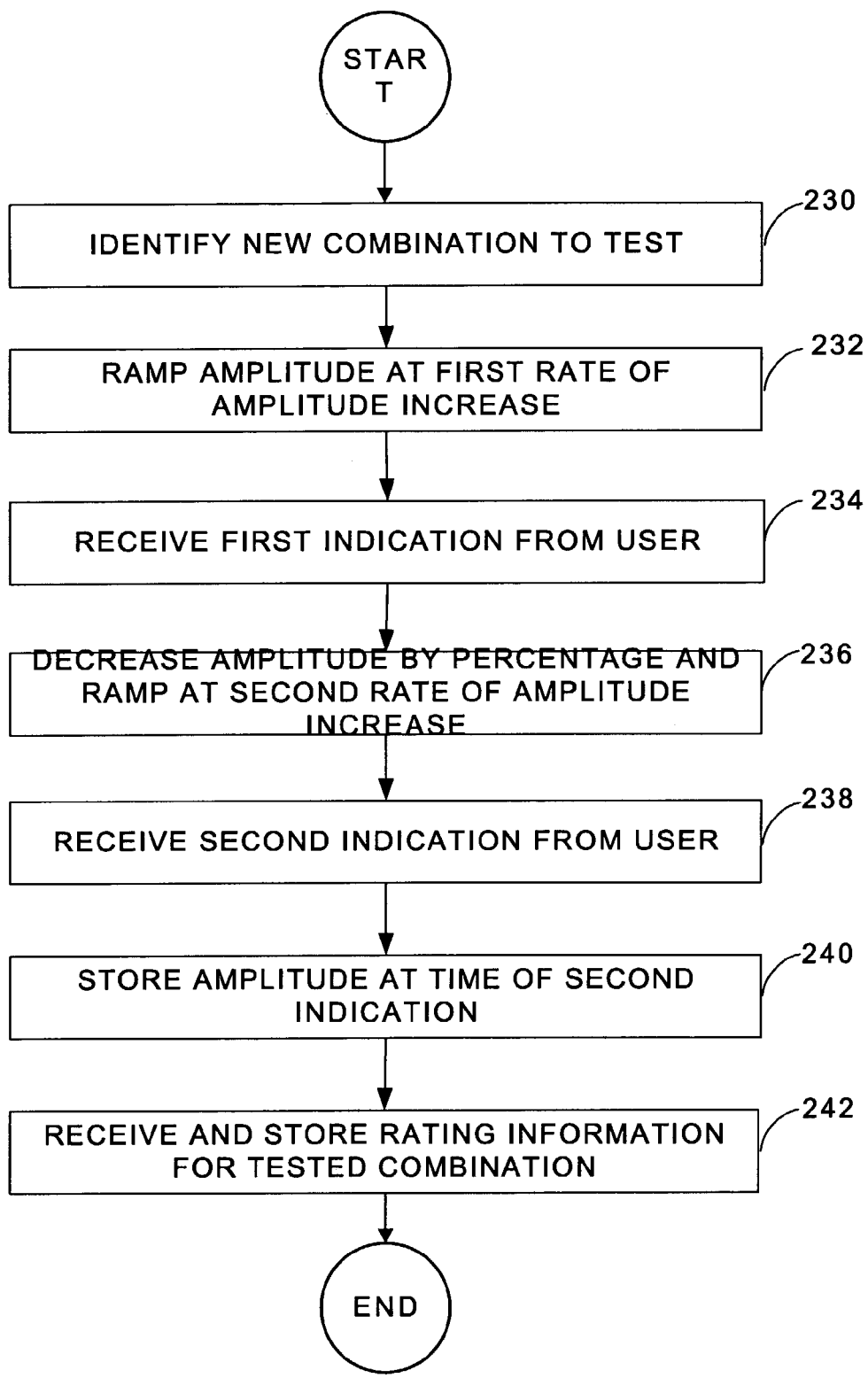
FIG. 7 is a flow diagram illustrating an example method that may be employed by a programming device to test an electrode combination according to the invention.

FIG. 7 is a flow diagram illustrating an example method that may be employed by programmer 20 to test an electrode combination according to the invention. Specifically, FIG. 7 illustrates a method that may be employed by programmer 20 each time a new electrode is tested as a first or additional cathode, or first or additional anode. In other words, FIG. 7 illustrates a method that may be employed by programmer 20 each time programmer 20 identifies a new electrode combination to test (230).

Programmer 20 controls IMD 14 to test the combination by controlling IMD 14 to deliver neurostimulation therapy via the combination. The clinician may select desired starting points for pulse amplitude, rate and width, and programmer 20 may ramp the amplitude from the starting point at a first rate of amplitude increase (232). Programmer 20 may increase the amplitude in, for example, a linear or step-wise fashion. In some embodiments, the clinician or patient 12 may control the rate of amplitude increase. The clinician or patient 12 stops the ramping of the amplitude when the stimulation causes discomfort, or other undesirable side effects (234).

Programmer 20 may reduce the amplitude at the time the ramp is stopped by some amount, e.g., a percentage, and ramps the amplitude again in order to allow the clinician and/or patient 12 to identify the amplitude that provides the best neurostimulation therapy (236, 238). This second time, programmer 20 may ramp the amplitude at a slower rate of amplitude increase in order to facilitate identification of the point where best neurostimulation is achieved. Again, in some embodiments, the clinician or patient 12 may control the amplitude.

Programmer 20 stores the amplitude at the time when the best neurostimulation therapy is indicated by the clinician and/or patient 12, and rating information for the combination (240, 242). The clinician and/or patient 12 may provide rating information, e.g., a numerical value for one or more metrics for rating the combination, which relates to the efficacy enabled by the combination or the side effects resulting from use of the combination, or both.

The clinician may use rating information and/or the amplitude values stored for each tested combination to identify desirable combinations. The combinations and their associated information and values may be presented in a list that may be ordered according to the information, the values, or a combination of the two. The amplitude value may, for example, be used to distinguish between tested combinations with similar ratings based on the power that must be consumed in order for each combination to enable desirable neurostimulation therapy.

Various embodiments of the invention have been described. However, one skilled in the art will appreciate that various additions and modifications can be made to these embodiments without departing from the scope of the invention. For example, although programmer 20 has been described herein as a hand-held computing device, programmer 20 may take the form of any type of computing device, such as a laptop or desktop computer, may access resources, such as memory 54, via a computer network, such as a LAN, WAN, or the World Wide Web. Further, programmer 20 may include a plurality of computing devices, which may communicate to provide the functionality ascribed to programmer 20 herein via a computer network.

Although described herein as associated with and interacting with a clinician, i.e., a clinician programmer, programmer 20 may be associated with patient 12, i.e., a patient programmer. In some embodiments, patient 12 may simply interact with programmer 20 in place of the clinician for some or all of the electrode combination identification process. In other embodiments, patient 12 may perform parts of the combination identification process without being supervised by the clinician, e.g., away from the clinic, using a patient programmer. These and other embodiments are within the scope of the following claims.

The invention claimed is:

1. A method comprising:
    selecting a first electrode of a set of electrodes implanted in a patient as a first cathode to include in a combination of electrodes for use in delivery of neurostimulation therapy to the patient;
    automatically selecting a sequence of additional electrodes of the set to test with the first cathode as a first anode for inclusion in the combination of electrodes based on decreasing proximity of the additional electrodes to the first cathode; and
    controlling an implantable medical device to deliver stimulation via a plurality of combinations of the set of electrodes implanted in the patient, each of the combinations including the first cathode and at least one of the additional electrodes.

2. The method of claim 1, wherein selecting a first electrode comprises receiving input from a user that identifies the first electrode.

3. The method of claim 1, wherein selecting a first electrode comprises:
    identifying an initial position within the set;
    controlling an implantable medical device to test one of the electrodes located at the initial position for inclusion in the combination as the first cathode; and
    controlling the implantable medical device to test additional electrodes of the set for inclusion in the combination as the first cathode in an order determined based on the initial position.

4. The method of claim 3, wherein identifying an initial position within the set comprises:
   identifying a configuration of the electrode set; and
   identifying the initial position based on the configuration.

5. The method of claim 3, wherein the initial position is a central position within the set, and controlling the implantable medical device to test additional electrodes comprises controlling the implantable medical device to test the additional electrodes in an order based on decreasing proximity of the additional electrodes to the initial position.

6. The method of claim 1, further comprising controlling an implantable medical device to test the additional electrodes according to the sequence.

7. The method of claim 6, wherein controlling an implantable medical device to test the additional electrodes comprises controlling the implantable medical device to test a plurality of combinations of electrodes, each of the combinations including the first cathode and at least one of the additional electrodes.

8. The method of claim 7, wherein controlling the implantable medical device to test a combination of electrodes comprises:
   controlling the implantable medical device to deliver neurostimulation via the combination of electrodes;
   controlling the implantable medical device to increase an amplitude of the neurostimulation until an indication to stop increasing the amplitude is received from a user;
   storing a value of the amplitude at a time when the indication is received from the user as an amplitude value for the combination; and
   storing rating information received from the user that describes at least one of the effectiveness of the delivery of neurostimulation at the stored amplitude value in addressing symptoms of the patient and a degree of side effects caused by delivery of neurostimulation at the stored amplitude value as rating information for the combination.

9. The method of claim 8, further comprising:
   displaying a list of the tested electrode combinations ordered according to at least one of amplitude values and rating information stored for each of the tested combinations;
   receiving a selection of one of the tested combinations made by the user from the list; and
   storing information identifying the selected combination as part of a neurostimulation therapy program that defines neurostimulation therapy to be delivered to the patient by the implantable medical device.

10. The method of claim 8, further comprising:
    selecting one of the tested combinations based on the information; and
    storing information identifying the selected combination as part of a neurostimulation therapy program that defines neurostimulation therapy to be delivered to the patient by the implantable medical device.

11. The method of claim 8, wherein the user is one of a clinician and the patient.

12. The method of claim 6, wherein controlling an implantable device to test the additional electrodes comprises:
    identifying a subset of undesignated electrodes within the set based on orientation of the undesignated electrodes with the first cathode and the first anode; and
    controlling the implantable medical device to test electrodes within the subset in an order based on decreasing proximity of the electrodes within the subset to the first cathode.

13. The method of claim 1, wherein the combination includes a most recently tested additional electrode, the method further comprising:
    identifying untested electrodes that would be tested after the most recently tested additional electrode according to the sequence; and
    storing information identifying additional combinations of electrodes that include the identified untested electrodes as part of neurostimulation therapy programs.

14. A computer-readable medium comprising instructions that cause a processor to:
    select a first electrode of a set of electrodes implanted in a patient as a first cathode to include in a combination of electrodes for use in delivery of neurostimulation therapy to the patient; and
    automatically select a sequence of additional electrodes of the set to test with the first cathode as a first anode for inclusion in the combination of electrodes based on decreasing proximity of the additional electrodes to the first cathode.

15. The computer-readable medium of claim 14, wherein the instructions that cause a processor to select a first electrode comprise instructions that cause a processor to receive input from a user that identifies the first electrode.

16. The computer-readable medium of claim 14, wherein the instructions that cause a processor to select a first electrode comprise instructions that cause a processor to:
    identify an initial position within the set;
    control an implantable medical device to test one of the electrodes located at the initial position for inclusion in the combination as the first cathode; and
    control the implantable medical device to test additional electrodes of the set for inclusion in the combination as the first cathode in an order determined based on the initial position.

17. The computer-readable medium of claim 14, wherein the instructions that cause a processor to identify an initial position within the set comprise instructions that cause a processor to:
    identify a configuration of the electrode set; and
    identify the initial position based on the configuration.

18. The computer-readable medium of claim 17, wherein the initial position is a central position within the set, and the instructions that cause a processor to control the implantable medical device to test additional electrodes comprise instructions that cause a processor to control the implantable medical device to test the additional electrodes in an order based on decreasing proximity of the additional electrodes to the initial position.

19. The computer-readable medium of claim 14, further comprising instructions that cause a processor to control an implantable medical device to test the additional electrodes according to the sequence.

20. The computer-readable medium of claim 19, wherein the instructions that cause a processor to control an implantable medical device to test the additional electrodes comprise instructions that cause a processor to control the implantable medical device to test a plurality of combinations of electrodes, each of the combinations including the first cathode and at least one of the additional electrodes.

21. The computer-readable medium of claim 20, wherein the instructions that cause a processor to control the implantable medical device to test a combination of electrodes comprise instructions that cause a processor to:
    control the implantable medical device to deliver neurostimulation via the combination of electrodes;

control the implantable medical device to increase an amplitude of the neurostimulation until an indication to stop increasing the amplitude is received from a user;

store a value of the amplitude at a time when the indication is received from the user as an amplitude value for the combination; and store rating information received from the user that describes at least one of the effectiveness of the delivery of neurostimulation at the stored amplitude value in addressing symptoms of the patient and a degree of side effects caused by delivery of neurostimulation at the stored amplitude value as rating information for the combination.

22. The computer-readable medium of claim 21, further comprising instructions that cause a processor to:

display a list of the tested electrode combinations ordered according to at least one of amplitude values and rating information stored for each of the tested combinations;

receive a selection of one of the tested combinations made by the user from the list; and store information identifying the selected combination as part of a neurostimulation therapy program that defines neurostimulation therapy to be delivered to the patient by the implantable medical device.

23. The computer-readable medium of claim 21, further comprising instructions that cause a processor to:

select one of the tested combinations based on the information; and store information identifying the selected combination as part of a neurostimulation therapy program that defines neurostimulation therapy to be delivered to the patient by the implantable medical device.

24. The computer-readable medium of claim 21, wherein the user is one of a clinician and the patient.

25. The computer-readable medium of claim 19, wherein the instructions that cause a processor to control an implantable medical device to test the additional electrodes comprise instructions that cause a processor to:

identify a subset of undesignated electrodes within the set based on orientation of the undesignated electrodes with the first cathode and the first anode; and control the implantable medical device to test electrodes within the subset in an order based on decreasing proximity of the electrodes within the subset to the first cathode.

26. The computer-readable medium of claim 14, wherein the combination includes a most recently tested additional electrode, further comprising instructions that cause a processor to:

identify untested electrodes that would be tested after the most recently tested additional electrode according to the sequence; and store information identifying additional combinations of electrodes that include the identified untested electrodes as part of neurostimulation therapy programs.

27. A device comprising a processor configured to select a first electrode of a set of electrodes implanted in a patient as a first cathode to include in a combination of electrodes for use in delivery of neurostimulation therapy to the patient, and configured to automatically selects a sequence of additional electrodes of the set to test with the first cathode as a first anode for inclusion in the combination of electrodes based on deceasing proximity of the additional electrodes to the first cathode.

28. The device of claim 27, wherein the processor receives input from a user that identifies the first electrode.

29. The device of claim 27, wherein the processor identifies an initial position within the set, controls the implantable medical device to test one of the electrodes located at the initial position for inclusion in the combination as the first cathode, and controls the implantable medical device to test additional electrodes of the set for inclusion in the combination as the first cathode in an order determined based on the initial position.

30. The device of claim 29, wherein the processor identifies a configuration of the electrode set, and identifies the initial position based on the configuration.

31. The device of claim 29, wherein the initial position is a central position within the set, and the processor controls the implantable medical device to test the additional electrodes in an order based on decreasing proximity of the additional electrodes to the initial position.

32. The device of claim 27, wherein the processor controls an implantable medical device to test the additional electrodes according to the sequence.

33. The device of claim 32, wherein the processor controls the implantable medical device to test a plurality of combinations of electrodes, each combination including the first cathode and at least one additional electrode.

34. The device of claim 33, further comprising a memory, wherein the processor controls the implantable medical device to test a combination of electrodes by controlling the implantable medical device to deliver neurostimulation via the combination of electrodes, controlling the implantable medical device to increase an amplitude of the neurostimulation until an indication to stop increasing the amplitude is received from a user, storing a value of the amplitude at a time when the indication is received from the user as an amplitude value for the combination in the memory, and storing rating information received from the user that describes at least one of the effectiveness of the delivery of neurostimulation at the stored amplitude value in addressing symptoms of the patient and a degree of side effects caused by delivery of neurostimulation at the stored amplitude value in the memory as rating information for the combination.

35. The device of claim 34, wherein the processor displays a list of the tested electrode combinations ordered according to at least one of amplitude values and rating information stored for each of the tested combinations, receives a selection of one of the tested combinations made by the user from the list, and stores information identifying the selected combination as part of a neurostimulation therapy program that defines neurostimulation therapy to be delivered to the patient by the implantable medical device.

36. The device of claim 34, wherein the processor selects one of the tested combinations based on the information, and stores information identifying the selected combination as part of a neurostimulation therapy program that defines neurostimulation therapy to be delivered to the patient by the implantable medical device.

37. The device of claim 32, wherein the processor identifies a subset of undesignated electrodes within the set based on orientation of the undesignated electrodes with the first cathode and the first anode, and controls the implantable medical device to test electrodes within the subset in an order based on decreasing proximity of the electrodes within the subset to the first cathode.

38. The device of claim 27, further comprising a memory, wherein the combination includes a most recently tested additional electrode, and the processor identifies untested electrodes that would be tested after the most recently tested additional electrode according to the order, and stores information identifying additional combinations of electrodes that include the identified untested electrodes as part of neurostimulation therapy programs in the memory.

39. The device of claim 27, wherein the device comprises a programming device associated with one of a clinician and the patient.

40. A method comprising:
selecting a first electrode of a set of electrodes implanted in a patient as a first cathode to include in a combination of electrodes for use in delivery of neurostimulation therapy to the patient;
automatically selecting a sequence of additional electrodes of the set to test with the first cathode as a first anode for inclusion in the combination of electrodes according to locations of the additional electrodes relative to the first cathode; and
controlling an implantable medical device to deliver stimulation via a plurality of combinations of the set of electrodes implanted in the patient, each of the combinations including the first cathode and at least one of the additional electrodes,
wherein selecting a first electrode comprises:
identifying an initial position within the set;
controlling an implantable medical device to test one of the electrodes located at the initial position for inclusion in the combination as the first cathode; and
controlling the implantable medical device to test additional electrodes of the set for inclusion in the combination as the first cathode in an order determined based on the initial position,
wherein the initial position is a central position within the set, and controlling the implantable medical device to test additional electrodes comprises controlling the implantable medical device to test the additional electrodes in an order based on decreasing proximity of the additional electrodes to the initial position.

41. A method comprising:
selecting a first electrode of a set of electrodes implanted in a patient as a first cathode to include in a combination of electrodes for use in delivery of neurostimulation therapy to the patient;
automatically selecting a sequence of additional electrodes of the set to test with the first cathode as a first anode for inclusion in the combination of electrodes according to locations of the additional electrodes relative to the first cathode;
controlling an implantable medical device to deliver stimulation via a plurality of combinations of the set of electrodes implanted in the patient each of the combinations including the first cathode and at least one of the additional electrodes; and
controlling an implantable medical device to test the additional electrodes according to the sequence, wherein controlling the implantable device to test the additional electrodes comprises:
identifying a subset of undesignated electrodes within the set based on orientation of the undesignated electrodes with the first cathode and the first anode; and
controlling the implantable medical device to test electrodes within the subset in an order based on decreasing proximity of the electrodes within the subset to the first cathode.

42. A computer-readable medium comprising instructions that cause a processor to:
select a first electrode of a set of electrodes implanted in a patient as a first cathode to include in a combination of electrodes for use in delivery of neurostimulation therapy to the patient; and
automatically select a sequence of additional electrodes of the set to test with the first cathode as a first anode for inclusion in the combination of electrodes according to locations of the additional electrodes relative to the first cathode,
wherein the instructions that cause a processor to identify an initial position within the set comprise instructions that cause a processor to:
identify a configuration of the electrode set; and
identify the initial position based on the configuration,
wherein the initial position is a central position within the set, and the instructions that cause a processor to control the implantable medical device to test additional electrodes comprise instructions that cause a processor to control the implantable medical device to test the additional electrodes in an order based on decreasing proximity of the additional electrodes to the initial position.

43. A computer-readable medium comprising instructions that cause a processor to:
select a first electrode of a set of electrodes implanted in a patient as a first cathode to include in a combination of electrodes for use in delivery of neurostimulation therapy to the patient;
automatically select a sequence of additional electrodes of the set to test with the first cathode as a first anode for inclusion in the combination of electrodes according to locations of the additional electrodes relative to the first cathode; and
control an implantable medical device to test the additional electrodes according to the sequence, wherein the instructions that cause a processor to control an implantable medical device to test the additional electrodes comprise instructions that cause a processor to:
identify a subset of undesignated electrodes within the set based on orientation of the undesignated electrodes with the first cathode and the first anode; and
control the implantable medical device to test electrodes within the subset in an order based on decreasing proximity of the electrodes within the subset to the first cathode.

44. A device comprising a processor configured to select a first electrode of a set of electrodes implanted in a patient as a first cathode to include in a combination of electrodes for use in delivery of neurostimulation therapy to the patient, and automatically selects a sequence of additional electrodes of the set to test with the first cathode as a first anode for inclusion in the combination of electrodes according to locations of the additional electrodes relative to the first cathode,
wherein the processor configured to identify an initial position within the set, controls the implantable medical device to test one of the electrodes located at the initial position for inclusion in the combination as the first cathode, and Controls the implantable medical device to test additional electrodes of the set for inclusion in the combination as the first cathode in an order determined based on the initial position, and
wherein the initial position is a central position within the set, and the processor controls the implantable medical device to test the additional electrodes in an order based on decreasing proximity of the additional electrodes to the initial position.

45. A device comprising a processor configured to select a first electrode of a set of electrodes implanted in a patient as a first cathode to include in a combination of electrodes for use in delivery of neurostimulation therapy to the patient, and automatically selects a sequence of additional electrodes of the set to test with the first cathode as a first anode for inclusion in the combination of electrodes according to locations Of the additional electrodes relative to the first cathode, wherein the processor configured to control an implantable medical device to test the additional electrodes according to the sequence, and wherein the processor configured to identify a subset of undesignated electrodes within the set based on orientation of the undesignated electrodes with the first cathode and the first anode, and controls the implantable medical device to test electrodes within the subset in an order based on decreasing proximity of the electrodes within the subset to the first cathode.

\* \* \* \* \*

UNITED STATES PATENT AND TRADEMARK OFFICE
CERTIFICATE OF CORRECTION

| | | |
|---|---|---|
| PATENT NO. | : 7,463,928 B2 | Page 1 of 1 |
| APPLICATION NO. | : 10/424194 | |
| DATED | : December 9, 2008 | |
| INVENTOR(S) | : Michael T. Lee | |

It is certified that error appears in the above-identified patent and that said Letters Patent is hereby corrected as shown below:

Column 15
"selects a" should read -- select a --.

Column 17
"patient each" should read -- patient, each --.

Signed and Sealed this

Twenty-sixth Day of May, 2009

JOHN DOLL
*Acting Director of the United States Patent and Trademark Office*